(12) United States Patent
Zeijlemaker

(10) Patent No.: US 9,020,610 B2
(45) Date of Patent: Apr. 28, 2015

(54) ELECTRODE SYSTEM WITH SHUNT ELECTRODE

(75) Inventor: Volkert A. Zeijlemaker, Landgraaf (NL)

(73) Assignee: Medtronic, Inc., Minneapolis, MN (US)

( * ) Notice: Subject to any disclaimer, the term of this patent is extended or adjusted under 35 U.S.C. 154(b) by 1649 days.

(21) Appl. No.: 11/426,207

(22) Filed: Jun. 23, 2006

(65) Prior Publication Data
US 2008/0009905 A1    Jan. 10, 2008

(51) Int. Cl.
*A61N 1/37* (2006.01)
*A61N 1/05* (2006.01)
*A61N 1/08* (2006.01)

(52) U.S. Cl.
CPC .............. *A61N 1/056* (2013.01); *A61N 1/057* (2013.01); *A61N 1/0573* (2013.01); *A61N 2001/086* (2013.01)

(58) Field of Classification Search
CPC . A61N 2001/086; A61N 1/3718; A61N 1/056
USPC ................................... 607/121, 122
See application file for complete search history.

(56) References Cited

U.S. PATENT DOCUMENTS

| | | | |
|---|---|---|---|
| 4,711,027 A | 12/1987 | Harris et al. | |
| 5,324,327 A * | 6/1994 | Cohen | 607/122 |
| 5,534,022 A * | 7/1996 | Hoffmann et al. | 607/122 |
| 6,871,091 B2 | 3/2005 | Wilkinson et al. | |
| 2002/0183817 A1 | 12/2002 | Van Venrooij et al. | |
| 2003/0083723 A1 | 5/2003 | Wilkinson et al. | |
| 2003/0083726 A1 * | 5/2003 | Zeijlemaker et al. | 607/122 |
| 2003/0144717 A1 | 7/2003 | Hagele | |
| 2003/0144718 A1 | 7/2003 | Zeijlemaker | |
| 2003/0144720 A1 | 7/2003 | Villaseca et al. | |
| 2003/0144721 A1 | 7/2003 | Villaseca et al. | |
| 2005/0070972 A1 | 3/2005 | Wahlstrand et al. | |
| 2005/0222642 A1 | 10/2005 | Przybyszewski et al. | |
| 2005/0222647 A1 | 10/2005 | Wahlstrand et al. | |
| 2005/0222656 A1 | 10/2005 | Wahlstrand et al. | |
| 2005/0222657 A1 | 10/2005 | Wahlstrand et al. | |

(Continued)

FOREIGN PATENT DOCUMENTS

| | | |
|---|---|---|
| EP | 0745354 A | 12/1996 |
| WO | 03063946 A2 | 8/2003 |

(Continued)

OTHER PUBLICATIONS

International Search Report, PCT/US2007/071161, Dec. 27, 2007, 6 Pages.

(Continued)

*Primary Examiner* — Tammie K Heller
(74) *Attorney, Agent, or Firm* — Michael J. Ostrom; Stephen W. Bauer

(57) ABSTRACT

Electrode systems that may be used with implantable medical devices such as a pacemaker, in addition to one or more conventional electrodes, include a shunt electrode. Under ordinary conditions, the shunt electrode has very little effect upon the operation of the electrode system. When high frequency current is delivered to the electrode system, however, the electrode system shunts a large share of the high frequency current to the shunt electrode. The shunt electrode, which includes a conducting material surrounded by an insulating layer, dissipates heat that may be caused by the high frequency current.

19 Claims, 4 Drawing Sheets

(56) References Cited

U.S. PATENT DOCUMENTS

| | | |
|---|---|---|
| 2005/0222658 A1 | 10/2005 | Hoegh et al. |
| 2005/0222659 A1 | 10/2005 | Olsen et al. |
| 2005/0288761 A1* | 12/2005 | Brabec et al. ................. 607/122 |
| 2006/0041294 A1 | 2/2006 | Gray |
| 2006/0200218 A1 | 9/2006 | Wahlstrand |
| 2006/0247684 A1 | 11/2006 | Halperin et al. |
| 2006/0247747 A1 | 11/2006 | Olsen et al. |
| 2006/0247748 A1 | 11/2006 | Wahlstrand et al. |

FOREIGN PATENT DOCUMENTS

| | | |
|---|---|---|
| WO | WO2006118640 A | 11/2006 |
| WO | WO2006118641 A | 11/2006 |

OTHER PUBLICATIONS (PCT/US2007/079112) PCT Notification of the International Search Report, Mailed Oct. 24, 2008, 8 pages.

* cited by examiner

ELECTRODE SYSTEM WITH SHUNT ELECTRODE

FIELD OF THE INVENTION

The invention relates to electrodes implantable in a human or animal body.

BACKGROUND OF THE INVENTION

Magnetic resonance imaging (MRI) techniques have been developed for various medical applications. MRI techniques make use of electromagnetic fields to create images of a patient. MRI techniques may allow for the generation of high-quality two- or three-dimensional images of a patient tissue, which can then be examined by a physician for diagnosis purposes. In particular, MRI techniques allow for the generation of internal images of patient's tissue, blood, flesh, organs, or the like, which can be examined to identify problems with the patient and facilitate improved patient care.

MRI devices typically subject a patient to a very strong magnetic field, and then apply pulses or bursts of radio frequency (RF) radiation to an area of the patient to be imaged. The strong magnetic field generally orients the protons of the tissue of the patient in particular directions. However, the RF bursts cause some of the patient's protons to resonate, or spin, at a particular frequency, depending on the local magnetic field. The resonance frequency is often referred to as the Larmour frequency, and has a linear relation with the local magnetic field. When the RF energy burst is terminated, the resonating protons reorient in accordance with the strong magnetic field of the MRI device, giving off energy in the process. The MRI device can detect the energy given off by the reorienting protons to create a high quality image of the patient tissue.

A wide variety of implantable medical devices (IMDs), including active implantable medical devices (AIMDs), have also been developed to monitor patient conditions or possibly deliver therapy to the patient. Some IMDs perform both monitoring and therapeutic functions. One common example of an IMD is a pacemaker. A pacemaker typically includes at least one pacing and sensing lead for sensing cardiac activity and delivery of pacing pulses to the heart. Other examples include implantable brain stimulators, implantable gastric system stimulators, implantable nerve stimulators or muscle stimulators, implantable lower colon stimulators, implantable drug or beneficial agent dispensers or pumps, implantable cardiac signal loops or other types of recorders or monitors, implantable gene therapy delivery devices, implantable incontinence prevention or monitoring devices, implantable insulin pumps or monitoring devices, and so on.

Conventionally, patients that use IMDs are generally discouraged or prohibited from being subjected to MRI. One of the concerns is that, during an MRI procedure, time-varying electromagnetic fields generated by the MRI device may cause energy to be transferred to leads associated with the IMD. It is desirable to overcome this limitation.

DETAILED DESCRIPTION OF THE INVENTION

Figure 1:
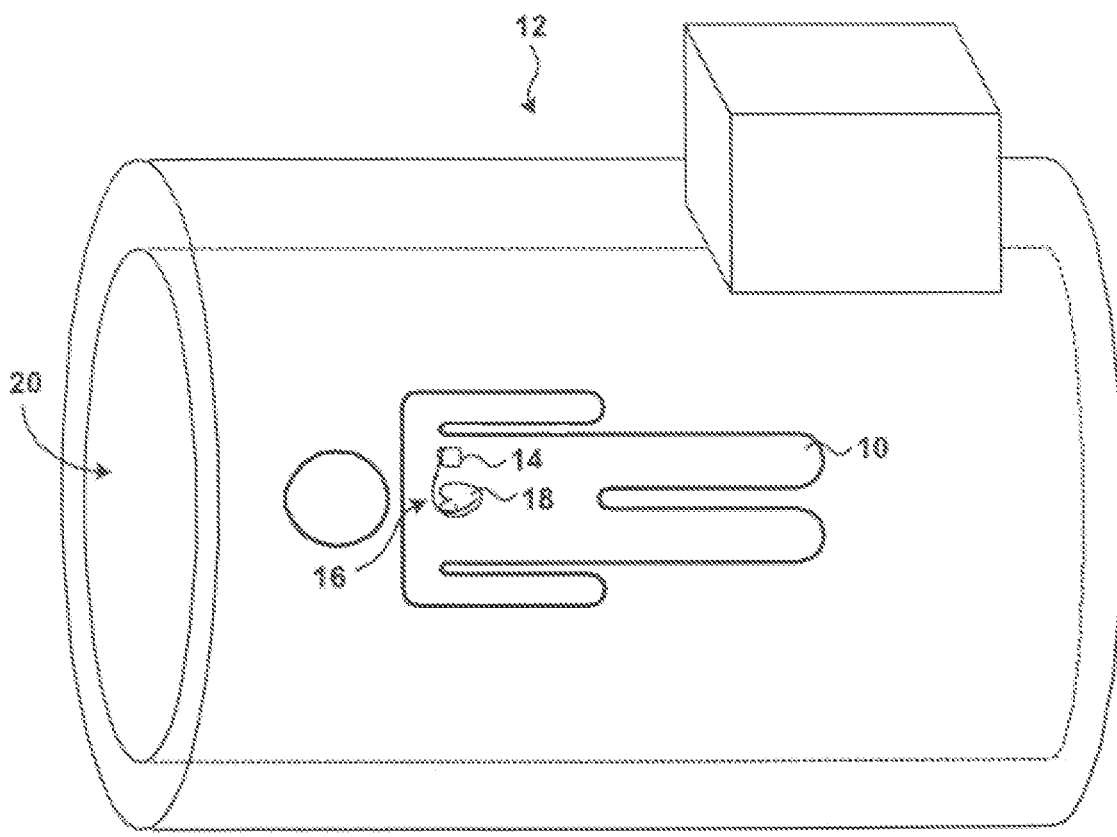
FIG. 1 is a conceptual diagram illustrating a magnetic resonance imaging (MRI) device and an implantable medical device (IMD) with leads employing the techniques of the invention.

In general, the claimed invention is directed to electrode systems that include a shunt electrode. The electrode systems behave in a conventional manner under ordinary conditions, such as ordinary stimulation and sensing, in which case the shunt electrode has very little effect upon the operation of the electrode system. When high frequency current is delivered to the electrode system, however, the electrode system shunts most of the high frequency current to the shunt electrode. The shunt electrode, which has a large surface area, dissipates the resulting heat.

The electrode system includes a conventional electrode for sensing signals, delivering stimulations, or both. The conventional electrode and the shunt electrode are coupled to the same conductor. As a result, electrical signals conducted along the lead and through patient tissue pass through the conventional electrode and the shunt electrode in parallel. The current divides among the conventional electrode and the shunt electrode according to current division principles, with the lower impedance path receiving more current.

The shunt electrode includes a conducting material surrounded by an insulating layer. Because the shunt electrode is separated from direct tissue contact by the insulating layer, the shunt electrode behaves like a capacitor. Accordingly, the impedance of the shunt electrode varies inversely with the frequency of the signals conducted through the electrode system. Therefore, the current division between the conventional electrode and the shunt electrode is a function of the frequency of the signals.

When the electrode system conducts low frequency signals, such as during ordinary pacing and sensing, the impedance of the shunt electrode is very high, and the current routed to the shunt electrode is negligible. When the electrode system conducts high frequency signals, such as high frequency signals induced in the lead by an MRI procedure, the high frequency impedance of the shunt electrode is very low, and more high frequency current is routed to the shunt electrode. The heating caused by this high frequency current is distributed over a larger surface area.

In one embodiment, the invention is directed to a device comprising a length of an electrical conductor and a first electrode coupled to the distal end of the conductor. The first electrode may be, for example, a conventional tip electrode. The device also includes a second electrode coupled to the conductor proximate to the first electrode. The second electrode serves as the shunt electrode. The second electrode comprises a conducting material and an insulating layer surrounding the conducting material, and includes a surface area that is substantially larger than the surface area of the first electrode. The second electrode may include, for example, a surface area that is twice as large or larger than the surface area of the first electrode. In some embodiments of the invention, the surface area of the second electrode may be four or more times larger than the surface area of the first electrode.

The insulating layer of the second electrode may include, for example, an applied dielectric coating, an oxide layer, a ceramic material, a synthetic sheath made materials such as silicone, or other non-conductive materials. The geometry of the second electrode may be controlled to regulate the capacitance of the second electrode. In one embodiment of the invention, the second electrode may have a capacitance of about 1 to 2 nanofarads.

The device may also include a third electrode, such as a conventional ring electrode. In this embodiment, the conductor may comprise a bipolar or multipolar conductor. In addition, the device may include a fixation mechanism to hold the electrodes in position relative to the tissue.

In another embodiment, the invention is directed to a lead for an implantable medical device comprising a conductor and first and second electrodes coupled to the conductor. The first electrode may be, for example, a conventional tip electrode and the second electrode may be a shunt electrode. The first and second electrodes form parallel conductive paths when placed in contact with tissue. The second electrode is so constructed to carry more current when high frequency current flows in the conductor and to carry less current when low frequency current flows in the conductor.

In a further embodiment, the invention is directed to a device comprising a length of an electrical conductor, a first electrode coupled to the conductor and a second electrode coupled to the conductor proximate to the first electrode. The second electrode is so constructed to have a capacitance of at least five picofarads. The second electrode may be constructed to have a larger capacitance, such as one to two nanofarads.

In an additional embodiment, the invention is directed to an implantable medical system. The system includes an elongated lead having a proximal end and a distal end, an implantable medical device coupled to the proximal end of the lead and an electrode system coupled to the distal end of the lead. The implantable medical device comprises a sensing module to detect electrical activity conducted by the lead or a current source to generate a stimulation conducted by the lead, or both. The second electrode comprises a conducting material and an insulating layer surrounding the conducting material. The second electrode includes a surface area that is substantially larger than the surface area of the first electrode.

The system may include a third electrode. The third electrode may be coupled to the lead, and may be an electrode such as a conventional ring electrode. The third electrode may also be coupled to the implantable medical device. A housing for the implantable medical device, for example, may include the third electrode. In one embodiment of the invention, the housing may include an uninsulated portion and an insulated portion, with the insulated portion serving as a second shunt electrode.

The claimed invention allows the patient to undergo an MRI procedure, or other procedures that may transmit high frequency energy to the body. The risk of heating from an MRI procedure is substantially reduced. The electrode systems are also compact and easily adaptable to many implantation.

The invention is directed to configurations or systems of one or more electrodes that may be used in a patient having an IMD such as a pacemaker. Each electrode may coupled to the IMD with a lead. The electrode may deliver electrical stimulations to tissue, or may sense electrical activity proximate to the tissue, or both. In the exemplary electrode configurations described below, the electrode may be implanted in the tissue of the heart, but the electrode may be implanted in any tissue and the invention is not limited to cardiac implantation.

Magnetic resonance imaging (MRI) techniques achieve a more effective image of the soft tissues of the heart and vascular system. Also, an MRI procedure can image these features without delivering a high dosage of radiation to the body of the patient, and as a result, MRI procedures may be repeated reliably and safely.

An MRI apparatus, however, uses time-varying electromagnetic fields that change at "radio frequencies," i.e., at frequencies in the radio range of the electromagnetic spectrum. Commercial MRI devices may operate at frequencies of about 10 MHz or higher. These high frequency fields cause energy to be transferred to the lead. In particular, the high frequency fields induce a voltage in the lead, causing the potential of the lead to be higher than the surrounding tissue. In effect, the lead behaves as an antenna. Current may flow from the electrode into the tissue proximate to the electrode due to induced voltage.

In contrast to radio frequency MRI signals, electrical stimulations delivered to the tissue by the electrode tend to be pulses at lower frequencies, several orders of magnitude below the frequency of MRI signals. The electrical signals generated or conducted by the tissue and sensed by the electrode are likewise low frequency signals. These low frequency signals are typically low-energy signals. The invention is directed to electrode configurations that respond differently to low frequency signals and high frequency signals. When the signal is a low frequency signal such as an IMD stimulation or an electrical signal originating from cell depolarizations, the electrode functions in a conventional manner. When the signal is a high frequency signal such as a signal caused by an MRI procedure or from other high frequency source, the electrode efficiently manages the energy.

FIG. 1 is a conceptual diagram of a patient 10 inside an MRI device 12. Patient 10 has an IMD 14, with leads 16 extending from IMD 14 to the heart 18. IMD 14 may include one or more sensing modules that detect electrical activity proximate to electrodes at the distal ends of leads 16. In addition or in the alternative, IMD 14 may include a current source such as a pulse generator that generates electrical stimulations. The stimulations may be delivered to the tissue of patient 10 via electrodes at the distal ends of leads 16.

By way of example, IMD 14 is illustrated as a cardiac pacemaker that senses activations and provides therapeutic stimulation to heart 18 via electrodes at the distal ends of leads 16. As described in more detail below, the radio frequency electromagnetic fields generated by MRI device 12 may induce a voltage in leads 16.

IMD 14 need not be a cardiac pacemaker. IMD 14 may generally comprise any of a wide variety of medical devices that can be implanted in the body of a human or other life form. For example, IMD 14 may alternatively take the form of an implantable cardioverter, an implantable defibrillator, an implantable cardiac pacemaker-cardioverter-defibrillator, an implantable monitor, or an implantable neural sensor or stimulator. In short, the electrode configurations described herein may find useful applications in any of a wide variety of IMDs.

MRI device 12 may assume a wide variety of shapes, sizes or configurations. In the illustrated example, MRI device 12 defines a relatively large tubular cavity 20 into which patient 10 can be placed during the MRI techniques. The invention may also be applied in cases in which MRI device 12 defines a much smaller cavity.

MRI device 12 makes use of electromagnetic fields to create images of patient 10. For example, MRI device 12 may subject patient 10 to very strong electromagnetic fields via one or more permanent magnets and electromagnetic elements located about cavity 20. MRI device 12 then applies pulses or bursts of electromagnetic radiation, typically radio frequency (RF) radiation, to an area of the patient 10 to be imaged. Commercial static magnetic fields may reach 1.5 tesla, with RF radiation of about 60 MHz. Some fields may have a lower magnetic flux density and employ RF radiation at lower frequencies, and some may have a higher magnetic flux density and employ higher frequencies. In general, stronger fields and higher frequencies may cooperate to produce improved image resolution, so some implementations of MRI device 12 may, for example, employ a field twice as strong and generate electromagnetic radiation at a frequency twice as high.

The high frequency radiation may induce a voltage in leads 16. The induced voltage causes current flow to the electrodes at the distal ends of insulated leads 16, and to conduct into the body of patient 10. The body of patient 10 provides a low impedance path for the current. The current flow also causes an increase in the temperature adjacent to the electrodes, which may lead to tissue ablation.

The invention is directed to electrode configurations or systems that reduce heat transfer to the tissue. In addition to a conventional electrode for pacing, sensing or both, an electrode system includes a shunt electrode. The shunt electrode conducts high frequency current and reduces the effects of heating. As a result, the electrode system operates normally when pacing or sensing, but harmlessly manages energy transferred by a high frequency signal such as a signal caused by an MRI procedure.

An MRI procedure is not the only event that may generate a high frequency voltage in leads 16. Some electrocautery procedures, for example, may use high frequency radiation. Consequently, the invention is not limited to application in an MRI procedure but may be used in other situations.

Figure 2A:
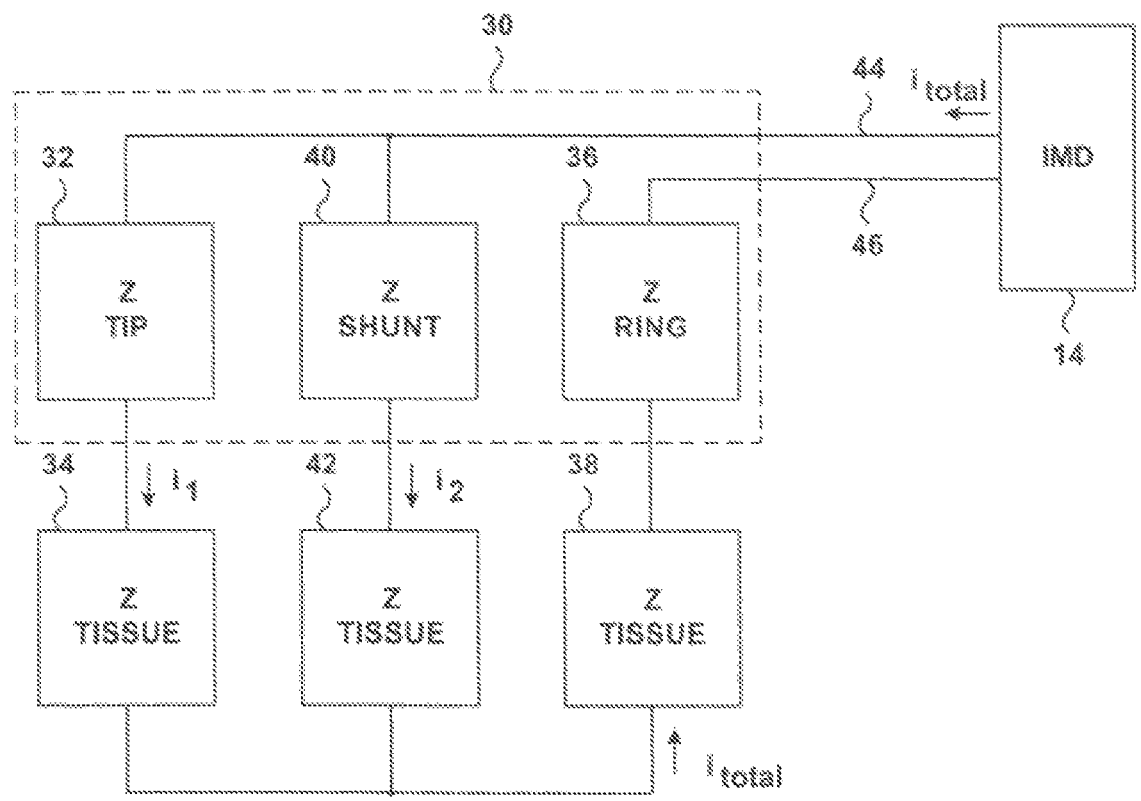
FIG. 2A is a circuit model of an implantable system including an IMD and a bipolar electrode system.

FIG. 2A is an electrical diagram of an implantable system, illustrating the operation of an electrode system 30. Each of the electrodes in electrode system 30 is modeled as an impedance. In addition, each of the electrodes in electrode system 30 is in contact with or proximate to tissue, and each tissue contact is modeled as an impedance.

Electrode system 30 comprises a conventional tip electrode 32 in direct contact with tissue site 34. The term "tip" is often used to denote an electrode with a small surface area at the distal end of a lead. The invention is not limited to electrodes placed at the distal end of a lead, however, and tip electrode 32 may encompass any kind of electrode placed anywhere on a lead.

Electrode system 30 may also include a conventional "ring" electrode 36 in contact with tissue site 38. A stimulus from IMD 14 may be delivered via tip electrode 32, with ring electrode 36 providing the return path for the stimulus current. In addition, IMD 14 may sense electrical activity between tip electrode 32 and ring electrode 36. The term "ring" is often used to denote an electrode located more proximally than the tip electrode. Such an electrode may be shaped like a ring, but the invention is not limited to electrodes having such a shape.

Electrode system 30 further comprises a shunt electrode 40 proximate to tissue site 42. The current path provided by shunt electrode 40 and tissue site 42 is in parallel to the current path provided by tip electrode 32 and tissue site 34. In particular, lead conductor 44 extends from IMD 14 to tip electrode 32 and shunt electrode 40, and current that passed through tip electrode 32 and shunt electrode 40 returns via return conductor 46. The total current between IMD 14 and tip and shunt electrodes 32, 40, denoted $i_{total}$, includes current induced in lead conductor 44, paced signals generated by IMD 14, and signals sensed from the tissue. The total current $i_{total}$ divides into two paths according to current division principles. The current through tip electrode 32 is denoted $i_1$ and current through shunt electrode 40 is denoted $i_2$. The magnitude of $i_1$ and the magnitude of $i_2$ are a function of the impedance of the respective current paths.

Unlike electrodes 32 and 36, which are in direct contact with tissue sites 34 and 38, shunt electrode 40 comprises a conducting material that is separated from tissue site 42 by a thin insulating layer. In some embodiments of the invention, shunt electrode 40 may also include a conductive layer surrounding the insulating layer, with the conductive layer interposed between tissue site 42 and the insulating layer. Because of the insulating layer, the electrical coupling between shunt electrode 40 and tissue site 42 includes a substantial reactive component. In other words, shunt electrode 40 behaves like a capacitor.

The impedance of a capacitor is inversely proportional to the frequency or frequencies of the current through it. The impedance encountered by current $i_2$, and consequently the division of current $i_{total}$, is therefore dependent upon the frequency or frequencies of the current signals represented by $i_{total}$. In particular, the impedance encountered by current $i_2$ is high for a low frequency signal, and low for a high frequency signal. When $i_{total}$ is a low frequency signal, the current path through shunt electrode 40 is a high impedance path, and by $i_2$ represents a negligible current flow. Electrical stimulations and sensed electrical signals, which are low frequency signals, therefore largely bypass, and are unaffected by, shunt electrode 40.

By contrast, MRI-induced signals, which are high frequency signals, tend to be diverted to shunt electrode 40. At high frequencies, shunt electrode 40 has a very low impedance, and $i_2$ is proportionately larger.

Tip electrode 32 has a comparatively small surface area. In some embodiments, tip electrodes may have a surface area of 1-4 square millimeters. In general, the smaller the tip electrode, the larger the impedance at the electrode. A tip electrode with a surface area of one square millimeter, for example, may have an impedance of about 1300 ohms. The increase in impedance that accompanies a decrease in surface area is desirable because a small tip electrode reduces the current drain on IMD 14, yet senses and paces well. A small tip electrode also may have a benefit of longevity.

When subjected to a high frequency signal such as a signal caused by an MRI procedure, however, a tip electrode with a small surface area may be unable to achieve dissipation of heat in a beneficial manner.

Shunt electrode 40, in contrast to tip electrode 32, has a substantially larger surface area. The surface area of shunt electrode 40 could be twice that of tip electrode 32, for example, but a larger ratio may generally offer better performance. In a typical embodiment, shunt electrode 40 may have at least four times the surface area of tip electrode 32. As a result, tissue contact site 42 is much larger than tissue contact site 34. The heating of shunt electrode 40 is a function of $i_2$ and the surface area of shunt electrode 40. In particular, the amount of heating is inversely related to the square of the surface area of shunt electrode 40. Increasing the surface area of shunt electrode 40 by four times, for example, would decrease the heating by a factor of sixteen. Because shunt electrode 40 has a large surface area, shunt electrode 40 distributes the heat over tissue contact site 42.

During ordinary operation, the signals conducted along lead conductor 44 and return path 46 are low frequency signals, and low frequency signals tend to avoid the current path through shunt electrode 40, because shunt electrode 40 has an impedance at low frequencies much higher than the impedance of tip electrode 32.

The predominant frequencies of pacing and sensing signals are usually well under 5 kilohertz, while a typical MRI procedure generates RF signals at about 64 megahertz. The impedance of a shunt electrode having a capacitance of 2 nanofarads, for example, would have a magnitude of over 15 kiloohms at 5 kilohertz. At low frequencies, therefore, the impedance of the shunt electrode is much larger than the impedance of a typical tip electrode.

When high frequency signals are induced in lead conductor 44, however, a substantial proportion of the high frequency current is diverted to shunt electrode 40, which has a lower impedance at high frequencies than tip electrode 32. The magnitude of the impedance of a 2 nanofarad shunt electrode at 64 megahertz would be about 1.2 ohms, significantly less than the impedance of a typical tip electrode. As a result, current $i_2$ is significantly larger at high frequencies than at low frequencies. Current $i_2$ causes shunt electrode 40 to become heated, but shunt electrode 40 distributes the heat along a large surface area.

Ring electrode 36 typically has a larger surface area than tip electrode 32. Accordingly, ring electrode 36 may safely distribute the heat generated by RF radiation without the need for a separate shunt electrode. The invention encompasses electrode systems, however, that include a second shunt electrode (not shown in FIG. 2) that provides a current path parallel to the current path provided by ring electrode 36 and tissue site 38.

Figure 2B:
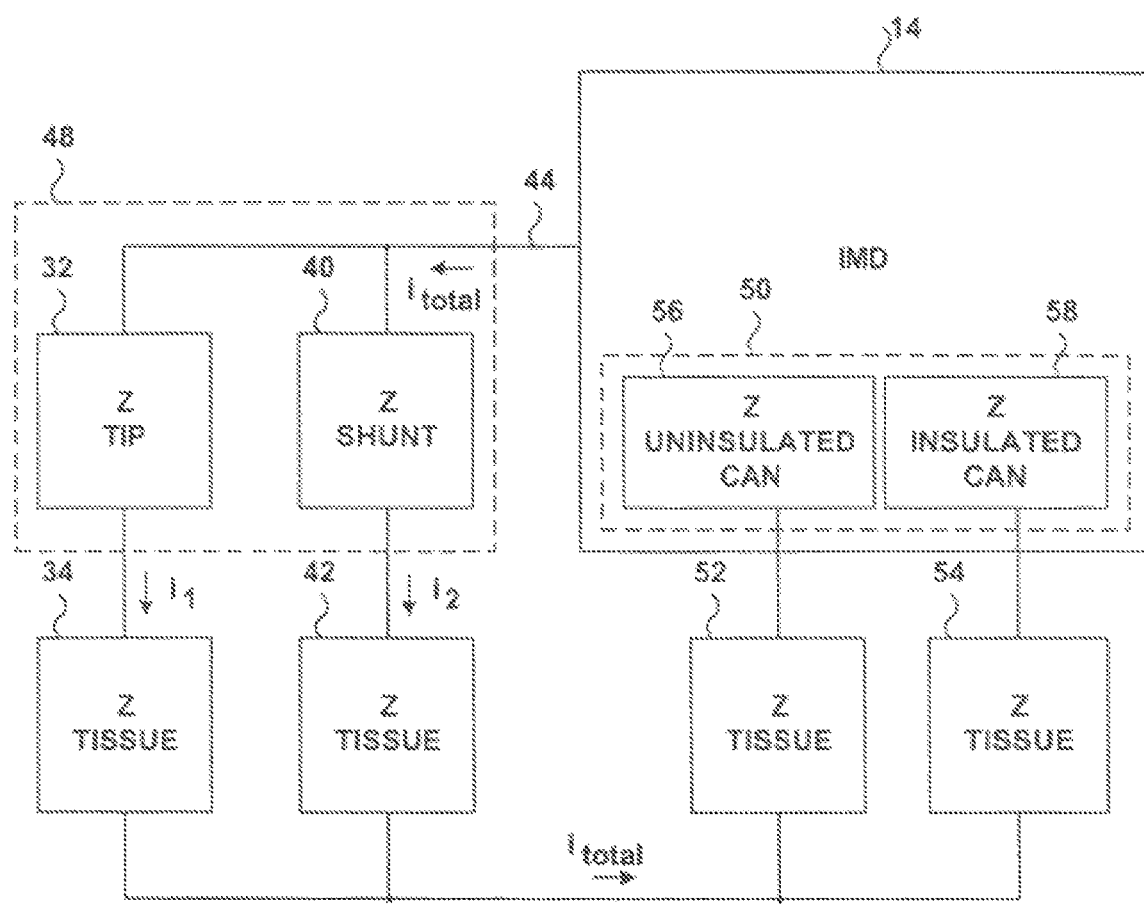
FIG. 2B is another circuit model of an implantable system including an IMD and a unipolar electrode system.

FIG. 2B is an electrical diagram illustrating an implantable system having a unipolar electrode system in accordance with an embodiment of the invention. The electrode system comprises a distal electrode set 48 and a proximal electrode set 50. FIG. 2B is similar to FIG. 2A in several respects. For example, distal electrode set 48 is similar to electrode system 30 shown in FIG. 2A, but does not include a ring electrode. Accordingly, the lead coupling distal electrode set 48 to IMD 14 may have a unipolar construction, including lead conductor 44 but not including return path conductor 46 as in FIG. 2A.

The return current path may be provided by the body tissue at contact sites 52, 54. Contact sites 52, 54 are in direct contact with proximal electrode set 50, which is embodied as "can" electrodes 56, 58 in the housing of IMD 14. Although IMD 14 may include a single conductive housing, an uninsulated portion of the housing 56 may be in direct contact with tissue 52, and another portion 58 may include a thin insulating layer. The insulating layer on the housing may be created or formed by any technique such as techniques described below. The surface area of insulated can electrode 58 may be substantially larger than the surface area of uninsulated can electrode 56.

The insulating layer on can electrode 58 causes the electrical coupling between insulated can electrode 58 and tissue site 54 to include a substantial reactive component. In other words, insulated can electrode 58 behaves as a shunt electrode for the return current path. Low frequency signals tend to avoid insulated can electrode 58, because insulated can electrode 58 has an impedance at low frequencies much higher than the impedance of uninsulated can electrode 56. High frequency signals, on the other hand, are more likely to return via insulated can electrode 58, and the resulting heat may be dissipated by the larger surface area of insulated can electrode 58.

In some embodiments of the invention, the uninsulated can electrode 56 may be configured to safely distribute the heat generated by RF radiation without the need for a separate shunt electrode. In such embodiments, insulated can electrode 58 may be unnecessary.

Figure 3:
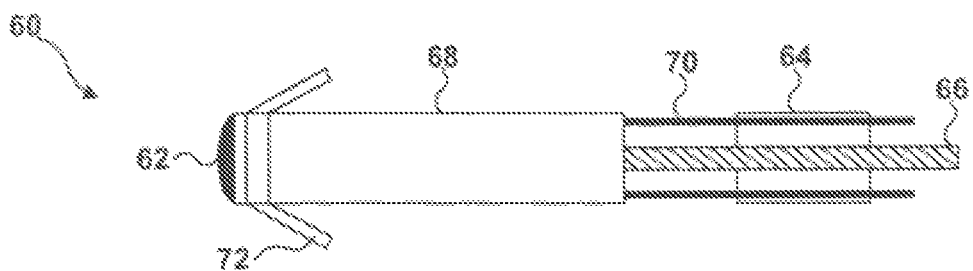
FIG. 3 is a side view of an exemplary electrode system, partially cut-away, showing construction of the electrode system in accordance with an embodiment of the invention.

FIG. 3 is a side view of an exemplary electrode system 60 constructed in accordance with an embodiment of the invention. Electrode system 60 comprises a conventional tip electrode 62 and a ring electrode 64. The diameter of electrode system 60 may be about 2 millimeters. The surface area of tip electrode 62 is significantly smaller than the surface area of ring electrode 64. Tip electrode 62 and ring electrode 64 may be formed from conventional corrosion-resistant and biocompatible materials.

Figure 4:
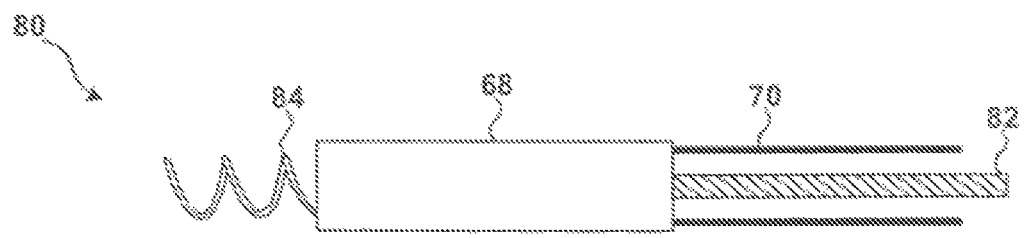
FIG. 4 is a side view of another exemplary electrode system, partially cut-away, showing construction of the electrode system in accordance with an embodiment of the invention.

A conventional conductor 66 electrically couples tip electrode 62 and ring electrode 64 to IMD 14 (not shown in FIG. 4). To provide a return path for electrical signals delivered by or sensed by IMD 14, conductor 66 may have a bipolar or multipolar construction. A bipolar conductor, for example, may include a first conducting element coupled to tip electrode 62 and a second co-axial conducting element coupled to ring electrode 64, thereby providing a return current path. In some embodiments of the invention, the conducting elements are conducting coils having one or more conducting wires per winding.

A shunt electrode 68 is electrically coupled to conductor 66 and to tip electrode 62, as shown in FIG. 2A. Shunt electrode 68 includes a conducting material surrounded by a thin insulating layer (not shown), which separates the conducting material of shunt electrode 68 from the tissue.

The insulating layer may be created or formed by any technique. For example, the layer may be created by applying a dielectric coating to the surface of shunt electrode 68. The layer may also be generated by forming shunt electrode 68 from a material such as tantalum or aluminum and "growing" a non-conductive oxide layer on the surface of shunt electrode 68. The layer may also include a ceramic material. The insulating layer may also comprise an encapsulation in a synthetic biocompatible material such as a sheath of silicone or other non-conductive material. The non-conductive layer may further comprise a combination of these techniques, such as an oxide layer surrounded by a silicone sheath.

The insulating layer may in turn be surrounded, partially or entirely, by an outer conductive layer, comprising a conductive substance such as platinum, titanium or tantalum. The insulating layer separates the conductive layer from the conducting material beneath the insulating layer. The conductive layer may enhance electrical contact with the tissue and the mechanical performance of shunt electrode 68. The invention includes embodiments with and without conductive layers.

Shunt electrode 68 may be about three to five millimeters long, giving shunt electrode 68 a surface area substantially larger than that of tip electrode 62. In general, shunt electrode 68 may be about four times as big as tip electrode 62, or larger. The dielectric and breakthrough properties of the insulating layer and the geometry of shunt electrode 68 can be controlled during the manufacturing process, and therefore the capacitance of shunt electrode 68 may be regulated. In some embodiments of the invention, for example, shunt electrode 68 may be manufactured to have a capacitance of approximately 1 to 2 nanofarads. Shunt electrode 68 may be constructed to have a larger or smaller capacitance. In some embodiments, the capacitance of shunt electrode 68 may be as low as five picofarads.

Electrode system 60 may be part of a lead that extends from IMD 14 (not shown) at the proximal end of the lead to tip electrode 62 at the distal end of the lead. Electrode system 60 and the lead may include insulative tubing 70 formed of a material such as polyurethane or silicone. The distal end of the lead includes a passive fixation mechanism, such as tines 72, that anchors electrode system 60 in place and helps hold electrode system 60 proximate to tissue. Other passive fixation mechanisms, such as fins or canted or curved structures, may also be employed.

FIG. 4 is a side view of an exemplary electrode system 80 constructed in accordance with another embodiment of the invention. Like electrode system 60 in FIG. 3, electrode system 80 includes a shunt electrode 68 and tubing 70. Shunt electrode 68 may be constructed as described above. Unlike electrode system 60, however, electrode system 80 does not include a ring electrode. Accordingly, conductor 82 may have a unipolar construction, and need not provide a return current path. The return current path may be provided by the body tissue and a can electrode in the housing of IMD 14.

Electrode system 80 further comprises an active fixation mechanism such as a fixed or extendable screw 84. Electrode system 80 may include a conventional steroid element (not shown) to assist in fixation. In addition to serving as a fixation mechanism, screw 84 may also serve as a tip electrode.

Figure 5:
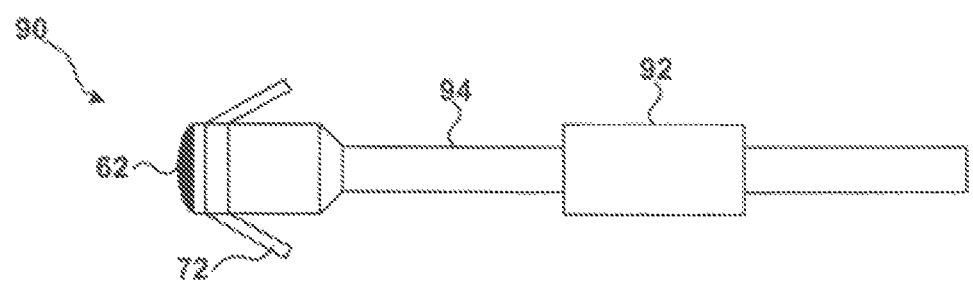
FIG. 5 is a side view of a further exemplary electrode system, showing construction of the electrode system in accordance with an embodiment of the invention.

FIG. 5 is a side view of an exemplary electrode system 90 constructed in accordance with another embodiment of the invention. Like electrode system 60 in FIG. 3, electrode system 90 includes standard tip electrode 62 and a passive fixation mechanism 72. Electrode system 90 does not include a ring electrode, however. Electrode system 90 includes a unipolar conductor (not shown in FIG. 5).

In electrode system 90, shunt electrode 92 is separated from tip electrode 62 by a small distance. A section of lead body 94, about ten millimeters long, separates shunt electrode 92 from tip electrode 62. Lead body section 94 may be constructed like an ordinary lead body, comprising a conductor surrounded by insulative tubing. Shunt electrode 92 also has a somewhat smaller surface area than shunt electrode 68 shown in FIGS. 3 and 4, but has a significantly larger surface area than tip electrode 62. Shunt electrode 92 may be constructed using techniques described above in connection with shunt electrode 68.

By distancing shunt electrode 92 from tip electrode 62, electrode system 90 may provide an added measure of protection against harmful tissue damage. In particular, should shunt electrode 92 become heated, the tissue affected by the heat will be removed from the tissue site in contact with tip electrode 62. As a result, the tissue proximate to tip electrode 62, which is used for pacing and sensing, is less likely to be damaged by the heat.

Under ordinary conditions, electrode systems such as those depicted in FIGS. 3-5 operate in a conventional manner. During conventional operation, current passing through the shunt electrode is negligible. When RF radiation induces current in the lead, the shunt electrode manages the current and dissipates the heat.

In addition, electrode systems such as those depicted in FIGS. 3-5 are compact and easily adaptable to many implantations known in the art. The construction of the shunt electrode may be incorporated in a variety of electrode system configurations, and is easily coupled to the lead conductor. The shunt electrode also consumes less space than conventional capacitors, allowing the electrode system to be inserted into a body with a conventional insertion apparatus such as a sheath, catheter or cannula.

For a patient having conventional electrodes, an MRI procedure may be contraindicated because of the risk of heating. A patient having an electrode system in accordance with the invention, however, may be eligible for an MRI procedure. The invention therefore makes MRI procedures more widely available. A patient with a heart condition will be able to obtain high quality images of his cardiac and vascular structures available through an MRI procedure, and need not be disqualified from MRI imaging merely because the patient has one or more electrodes disposed in his heart.

A number of embodiments of the invention have been described. However, one skilled in the art will appreciate that the invention can be practiced with embodiments other than those disclosed. For example, the invention is not limited to the exemplary electrode systems depicted in FIGS. 3-5. For example, the tip electrode and shunt electrode may be embodied in a single-piece construction, with an uninsulated portion serving as the tip electrode and an insulating layer surrounding the shunt electrode.

In addition, the invention encompasses ranges of capacitance of the shunt electrode. The selected capacitance of a shunt electrode may depend in part upon the selected impedance of the tip electrode. The disclosed embodiments are presented for purposes of illustration and not limitation, and the invention is limited only by the claims that follow.

The invention claimed is:

1. A lead for an implantable medical device, the lead comprising:
   a conductor;
   a first electrode electrically coupled to the conductor; and
   a second electrode electrically coupled to the conductor, wherein the second electrode comprises a conducting material and an insulating layer covering an outer portion of the conducting material such that the insulating material separates the entire outer portion of the conducting material of the second electrode from tissue when implanted,
   wherein the first and second electrodes coupled to the conductor form parallel conductive paths from the conductor to tissue when placed in contact with tissue, and wherein the first electrode and the second electrode are configured such that the second electrode carries more high frequency current than the first electrode when high frequency current at about 10 MHz or higher flows in the conductor and the first and second electrodes are placed in contact with tissue and such that the second electrode carries less low frequency current than the first electrode when low frequency current at frequencies below 5 KHz flows in the conductor and the first and second electrodes are placed in contact with tissue.

2. The lead of claim 1, wherein the insulating layer comprises at least one of an applied dielectric coating, an oxide layer, a ceramic material and a non-conductive synthetic sheath.

3. The lead of claim 1, wherein the first electrode has a first surface area and the second electrode has a second surface area, and wherein the second surface area is at least four times larger than the first surface area.

4. The lead of claim 1, further comprising a lead body section disposed between the first electrode and the second electrode.

5. The lead of claim 1, wherein the second electrode has a capacitance of about one to two nanofarads.

6. The lead of claim 1, wherein the second electrode further comprises a conductive layer surrounding the insulating layer, the conductive layer being interposed between the insulating layer and tissue when the first and second electrodes are placed in contact with tissue.

7. The lead of claim 6, wherein the conductive layer comprises at least one of platinum, titanium and tantalum.

8. The lead of claim 1, wherein the lead further comprises an additional conductor and a third electrode coupled to the additional conductor.

9. The lead of claim 1, wherein a proximal end of the conductor is configured to be coupled to an implantable medical device.

10. A lead for an implantable medical device, the lead comprising:
a conductor;
a first electrode electrically coupled to the conductor; and
a second electrode coupled to the conductor and the first electrode, wherein the second electrode comprises conducting material electrically coupled to the conductor and an insulating layer surrounding the conducting material such that an entire outer portion of the conducting material of the second electrode is separated from tissue when the first and second electrodes are placed in contact with tissue,
wherein the first and second electrodes coupled to the conductor form parallel conductive paths between the conductor and tissue when the first and second electrodes are placed in contact with tissue such that the second electrode carries more high frequency current than the first electrode when high frequency current is induced in the conductor by high frequency fields of about 10 MHz or higher and the first and second electrodes are placed in contact with tissue and such that the second electrode carries less low frequency current than the first electrode when low frequency current at frequencies below 5 KHz flows in the conductor and the first and second electrodes are placed in contact with tissue.

11. The lead of claim 10, wherein the second electrode has a capacitance of about one to two nanofarads.

12. The lead of claim 10, wherein the second electrode further comprises a conductive layer surrounding the insulating layer, the conductive layer being interposed between the insulating layer and tissue when the first and second electrodes are placed in contact with tissue.

13. The lead of claim 12, wherein the conductive layer comprises at least one of platinum, titanium and tantalum.

14. The lead of claim 10, wherein the first electrode is a tip electrode provided at a distal end of the lead.

15. The lead of claim 14, wherein a surface area of the first electrode is approximately one square millimeter.

16. The lead of claim 15, wherein the first electrode has a first surface area and the second electrode has a second surface area, and further wherein the second surface area is at least four times larger than the first surface area.

17. The lead of claim 10, wherein the lead further comprises an additional conductor and a third electrode coupled to the additional conductor.

18. The lead of claim 10, wherein the lead further comprises a lead body section disposed between the first electrode and the second electrode.

19. The lead of claim 18, wherein the lead body section is approximately 1 cm in length.

* * * * *